United States Patent
O'Lenick, Jr. et al.

(10) Patent No.: US 6,881,710 B1
(45) Date of Patent: Apr. 19, 2005

(54) PERSONAL CARE PRODUCTS BASED UPON SURFACTANTS BASED UPON ALKYL POLYGLUCOSIDE QUATERNARY COMPOUNDS

(75) Inventors: Anthony J. O'Lenick, Jr., Dacula, GA (US); Dean A. Smith, Chattanooga, TN (US); David Anderson, Chatt, TN (US)

(73) Assignee: Colonial Chemical Inc., South Pittsburg, TN (US)

( * ) Notice: Subject to any disclaimer, the term of this patent is extended or adjusted under 35 U.S.C. 154(b) by 0 days.

(21) Appl. No.: 10/792,613

(22) Filed: Mar. 4, 2004

(51) Int. Cl.[7] .............................. C11D 1/62; C11D 3/22
(52) U.S. Cl. ...................... 510/123; 510/119; 510/470; 510/504
(58) Field of Search ................................ 510/119, 123, 510/470, 504

(56) References Cited

U.S. PATENT DOCUMENTS 6,592,856 B1    7/2003    Giles et al.
6,627,612 B1 *   9/2003    O'Lenick et al. ............. 514/25

OTHER PUBLICATIONS

Colonial Chemical Website, "Sugaquats".*

* cited by examiner

Primary Examiner—Charles Boyer

(57) ABSTRACT

The present invention relates to personal care products based upon a novel series of polyglucoside quarternary compounds. These materials are surprisingly, extremely effective multi-functional surfactants used in shampoos and body wash products, providing the possibility of making a personal care product with only one surfactant. These unique products provide detergency, foam, conditioning, antimicrobial activity, wetting properties of formulations in a single molecule, and are derived from natural sugar compounds.

18 Claims, No Drawings

PERSONAL CARE PRODUCTS BASED UPON SURFACTANTS BASED UPON ALKYL POLYGLUCOSIDE QUATERNARY COMPOUNDS

FIELD OF THE INVENTION

The present invention relates to personal care products based upon a novel series of polyglycoside quaternary compounds. These materials are surprisingly, extremely effective multi-functional surfactants used in shampoos and body wash products, providing the possibility of making a personal care product with only one surfactant. These unique products provide detergency, foam, conditioning, antimicrobial activity, wetting properties to formulations in a single molecule, and are derived from natural sugar compounds.

Commercial formulations for shampoos contain a combination of ingredients. These include detergent, which are used to cleanse, an alkanolamid to improve foam, a preservative to prevent microbial contamination and a conditioning agent to improve the feel of the hair and wet comb properties. Each component has a specific function with little or no product crossover. Detergents, used to cleanse, are anionic surfactants selected from the group consisting of sulfates, ether sulfates, and alpha olefin sulfonate. This class of compounds de-fats as it cleanses and is generally quite irritating to the eyes and skin. Alkanolamid are added to improve foam density. These products are generally based upon diethanolamine and are subject to the formation of cancer suspect agents called nitrosamines. Preservatives, added to prevent microbial contamination, are likewise rather irritating and more and more are being shunned as not suitable for personal care products. In years gone by, formaldehyde was acceptable. The number of cosmetically acceptable preservatives shrinks each year and the concept of a truly selectively toxic preservative has been quite elusive. By selectively toxic is meant a preservative that is toxic to microbes, but non-toxic to people. Conditioning agents, used to improve the feel of the hair and wet comb properties of the hair, are generally quaternary nitrogen compounds. These materials are generally incompatible with anionic surfactants, forming insoluble salts. There are also a plethora of other ingredients optionally added including fragrances, actives, botanicals, silicones, thickening polymers and many others. It would be ideal to have a truly multi-functional surfactant that has all these desirable properties in one compound. Until the current compositions, such a product was not available.

BACKGROUND

U.S. Pat. No. 6,592,856 issued Jul. 15, 2003 to Giles et al is typical of shampoo systems. It discloses: "Hair conditioning shampoo compositions are provided which contain a combination of conditioning agents including emulsified silicones, cationic polymers and certain fatty acid polyesters of polyols. Suitable fatty acid polyesters are sucrose pentalaurate, sucrose tetraoleate, sucrose pentaerucate, sucrose tetraerucate, sucrose tetrastearate, sucrose pentaoleate, sucrose octaoleate, sucrose pentatallowate, sucrose trirapeate, sucrose tetrarapeate, sucrose pentarapeate, sucrose tristearate and sucrose pentastearate, and mixtures thereof. The compositions give improved hair conditioning benefits, especially to hair, which has been damaged, e.g. through environmental exposure or harsh mechanical or chemical treatments such as heat styling, perming or bleaching.

There are a number of essential elements in the U.S. Pat. No. 6,592,856 product. The patent claims: "An aqueous shampoo composition comprising: i) at least one cleansing surfactant chosen from anionic, zwitterionic and amphoteric surfactants or mixtures thereof, and; ii) a combination of conditioning agents including: (a) emulsified particles of an insoluble silicone; and (b) a cationic polymer; and and (c) a fatty acid polyester of a polyol selected from the group consisting of sucrose pentaerucate, sucrose tetraerucate and mixtures thereof.

U.S. Pat. No. 6,444,628 issued Sep. 3, 2002 to Nocerino, et al. discloses an "aqueous shampoo composition comprising, in addition to water an anionic cleansing surfactant, a cationic polymer, and a monoalkyl quaternary ammonium compound in which the alkyl chain length is C8 to C14. Again, the same type of formulation ingredients.

U.S. Pat. No. 6,221,817 issued Apr. 24, 2001 to Guskey, et al. discloses a "aqueous hair conditioning shampoo compositions comprising a specific surfactant component comprising an ethoxylated alkyl sulfate surfactant having from about 1 to about 8 moles of ethoxylation and an amphoteric surfactant in a shampoo with insoluble, dispersed conditioning agent, a low viscosity organic conditioning oil and a select soluble cellulosic cationic organic polymer hair conditioning agent".

Common to each of these recently issued patents on conditioning shampoos is the multitude of essential ingredients needed to obtain cleansing, foam improvement and conditioning effects. The present invention provides conditioning shampoos with one surfactant ingredient having all of the attributes sought in these other inventions. The formulations of the art are both multi-component and complicated. This approach in fact teaches away from our very simplistic approach. The art generally teaches that more is better. That is the more ingredients added, the better the formulation as relates to conditioning, detergency, foam, antimicrobial and other desirable properties. What out invention teaches is that less is better. That less coming from one unique natural surfactant that provides all the needed benefits in a single molecule.

THE INVENTION

SUMMARY OF THE INVENTION

The present invention is drawn to a composition for a multifunctional surfactant composition that provides cleaning, foam, conditioning, and preservation with one ingredient. This extraordinary combination of properties comes from a unique class of alkyl polyglucoside quaternary compounds that provide all of these desirable functionalities to a personal care product like shampoos and body wash.

DETAILED DESCRIPTION OF THE INVENTION

Specifically the present invention describes a process for cleansing and conditioning hair and skin with a self preserving composition which comprises contacting the hair and skin with an aqueous solution a composition conforming to the following:

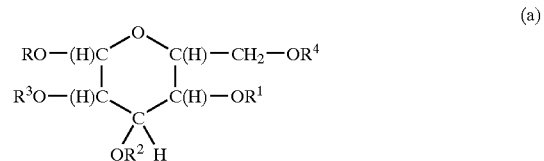
(a)

wherein;
R is alkyl having 8 to 22 carbon atoms;
$R^1$, $R^2$, $R^3$ and $R^4$ are independently selected from the group consisting of

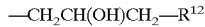

and H, with the proviso that $R^1$, $R^2$, $R^3$, and $R^4$ are not all H;
$R^{12}$ is

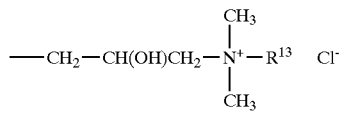

$R^{13}$ is alkyl having 8 to 22 carbon atoms, and

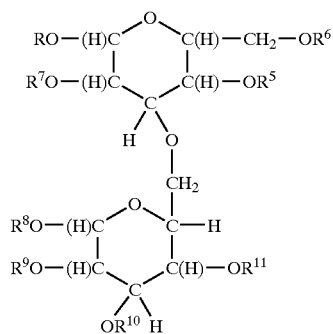

wherein;
R is alkyl having 8 to 22 carbon atoms;
$R^1$, $R^2$, $R^3$ and $R^4$, $R^5$, $R^6$, $R^7$, $R^8$, $R^9$, $R^{10}$, and $R^{11}$ are independently selected from the group consisting of

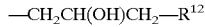

and H, with the proviso that $R^1$, $R^2$, $R^3$ and $R^4$ are not all H;
$R^{12}$ is

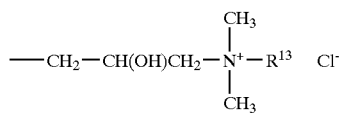

$R^{13}$ is alkyl having 8 to 22 carbon atoms.
Preferred Embodiment
In a preferred embodiment, $R^{13}$ is alkyl having 12 carbon atoms.
In a preferred embodiment, $R^{13}$ is alkyl having 16 carbon atoms.
In a preferred embodiment, $R^{13}$ is alkyl having 16 carbon atoms.
In a preferred embodiment, $R^{13}$ is alkyl having 18 carbon atoms.
In a preferred embodiment, $R^{13}$ is alkyl having 20 carbon atoms.
In a preferred embodiment, $R^{13}$ is alkyl having 22 carbon atoms.
In a preferred embodiment, $R^{13}$ is alkyl having 24 carbon atoms.
In a preferred embodiment, the effective concentration ranges from 1% to 25% by weight.

EXAMPLES

SugaQuats™

SugaQuats™ are products commercially available from Colonial Chemical Inc, South Pittsburg Tenn. SugaQuat™ is a trademark of Colonial Chemical Inc. They are 35% aqueous solutions of compositions conforming to the following structures:

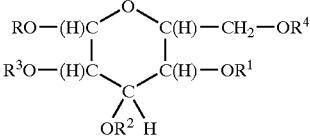

(a)

wherein;
R is alkyl having 8 to 22 carbon atoms;
$R^1$, $R^2$, $R^3$ and $R^4$ are independently selected from the group consisting of

and H, with the proviso that $R^1$, $R^2$, $R^3$, and $R^4$ are not all H;
$R^{12}$ is

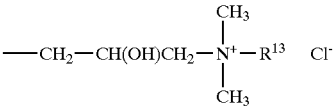

$R^{13}$ is alkyl having 8 to 22 carbon atoms, and

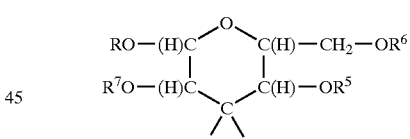

(b)

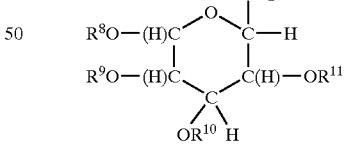

wherein;
R is alkyl having 8 to 22 carbon atoms;
$R^1$, $R^2$, $R^3$ and $R^4$, $R^5$, R, $R^7$, $R^8$, $R^9$, $R^{10}$, and $R^{11}$ are independently selected from the group consisting of

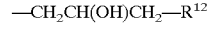

and H, with the proviso that $R^1$, $R^2$, $R^3$ and $R^4$ are not all H;

$R^{12}$ is

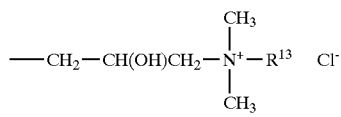

$R^{13}$ is alkyl having 8 to 20 carbon atoms.

Raw Material Examples

| Example | R | $R^{13}$ |
| --- | --- | --- |
| 1 | 8 | 22 |
| 2 | 10 | 20 |
| 3 | 12 | 18 |
| 4 | 12 | 12 |
| 5 | 14 | 16 |
| 6 | 16 | 12 |
| 7 | 18 | 14 |
| 8 | 20 | 8 |
| 9 | 22 | 10 |

Compositions of the Present Invention

The compositions of the present invention contain water and the products of Examples 1–9. The concentrations range from 1%–25% by weight with the preferred embodiment for concentration is between 5% and 15% by weight in water. The examples are 5% aqueous solutions of the compositions of the present invention.

| Example | SugaQuat Example | Water Grams | Grams |
| --- | --- | --- | --- |
| 10 | 1 | 10.0 | 60.0 |
| 11 | 2 | 10.0 | 60.0 |
| 12 | 3 | 10.0 | 60.0 |
| 13 | 4 | 10.0 | 60.0 |
| 14 | 5 | 10.0 | 60.0 |
| 15 | 6 | 10.0 | 60.0 |
| 16 | 7 | 10.0 | 60.0 |
| 17 | 8 | 10.0 | 60.0 |
| 18 | 9 | 10.0 | 60.0 |

Applications Testing

The above simple compositions were tested as conditioning shampoos and were found to have an excellent combination of properties. These include detergency, foam, conditioning, preservation and ocular mildness properties. This combination of properties from one multi-functional surfactant has been heretofore impossible to achieve with one material.

Foam

Sodium Lauryl sulfate is one of the most commonly used anionic surfactants. While it is a good detergent and produces large volume of foam, it is irritating and has no conditioning properties. In fact, it strips the oil from hair leaving the hair dry and fly away. Compounds of the present invention compare favorably with sodium lauryl sulfate in foam levels, and detergency, but also are non-irritating, conditioning and provide self-preserving properties. This coupled with the fact that they are derived from natural sugars, makes them the perfect single surfactant for personal care formulation. The following compounds were evaluated at 1% active in water. The higher the foam, the better.

Methodology

The foaming properties of the compositions were also evaluated by a modified "Ross-Miles Foam Test". This compares the foaming tendencies of different products or surfactants in water at various temperatures. The method was used to demonstrate and evaluate foaming tendency of products/treatment dosages.

The test is carried out as follows:

1. 500 ml. of water (the water should be representative of the system.sup.1) was added to a 1000 ml. graduated cylinder having a cylinder diameter 65 mm. Then 18.0-ppm ortho phosphate is added to the cylinder as a buffer. The test is carried out at a temperature of 66° C. to 67° C.
2. The concentration tested was 1% by weight solids.
3. Then cylinder with contents is shaken vertically at the specified temperature ten times (the times shaken equals the number of cycles). After the tenth time, the initial foam height (t=0) is recorded in ml. Then the foam level at t=5 minutes and t=30 minutes is recorded.

Results

| Product Evaluated | Foam Level |
| --- | --- |
| Sodium Lauryl Sulfate | 900 ml |
| Example 3 | 890 ml |
| Example 4 | 860 ml |
| Sodium laureth 2 sulfate | 770 ml |
| Example 7 | 760 ml |
| Sodium laureth 1-sulfate | 750 ml |
| Sodium laureth 3-sulfate | 720 ml |
| Example 8 | 720 ml |
| APG (from which Examples are derived) | 260 ml |

As can be easily seen the compositions of the present invention are excellent foaming compounds, comparable in all regards to the most commonly used surfactants in personal care products. As will be seen, unlike these commonly used surfactants the compositions of the present invention also provide conditioning, antimicrobial properties are non-irritating and are derived from natural products.

Conditioning

Conditioning was studied. The wet comb properties of hair washed in the salon in half head studies was conducted. Evaluation of the dry hair was also evaluated. A 5% solution of the composition of the present invention was evaluated. The person having the test run was asked to evaluate the following samples for combability and softness of the hair. The scale was 1 (poor) to 5 excellent.

| Material | Conditioning | Wet Comb |
| --- | --- | --- |
| Sodium Lauryl Sulfate | 1 | 1 |
| Sodium Laureth 2 Sulfate | 1 | 1 |
| Example 3 | 4 | 4 |
| Example 4 | 4 | 3 |
| Example 8 | 4 | 4 |
| Example 9 | 4 | 4 |
| Example 7 | 4 | 4 |
| APG (Raw material for preparation of the products of the current invention) | 2 | 2 |

As can be easily seen the compositions of the present invention are excellent conditioners, and provide outstanding both in wet comb properties. The commonly used surfactants provide no conditioning and no wet comb improvement. Additionally they are have no antimicrobial properties are irritating and are not derived from natural products.

Preservation

A study was conducted to determine the antimicrobial capability of four (4) SugaQuat (alkyl polyglucoside) variations utilizing the zone inhibition technique. The test materials were evaluated for gross antimicrobial activity against a series of four (4) test organisms: *Pseudomonas aeruginosa* (Gram-negative bacteria); *Staphylococcus aureus* (Gram-positive bacteria); *Candida albicans* (yeast) and *Aspergillus niger* (mold) utilizing the zone inhibition technique. Results of the assays are presented below.

Test Samples

Sodium Lauryl Sulfate (0.50% by weight concentration in water).

Sodium Laureth 2 Sulfate (0.50% by weight concentration in water).

Example 3 (0.50% by weight concentration in water).

Example 4 (0.50% by weight concentration in water).

Example 8 (0.50% by weight concentration in water).

Example 9 (0.50% by weight concentration in water).

Example 7 (0.50% by weight concentration in water).

Activity Summary

SCORING:

1=Excellent; 2=Very Good; 3=Good; 4=OK (moderate); 6=Poor; 8=No Activity

Control Compounds

| SAMPLE | Sa | Psa | Ca | An | Score | Comments |
|---|---|---|---|---|---|---|
| Sodium Lauryl Sulfate | 8 | 8 | 8 | 8 | 32 | No activity |
| Sodium Laureth 2 Sulfate | 8 | 8 | 8 | 8 | 32 | No activity |

Compositions of the Present Invention

| SAMPLE | Sa | Psa | Ca | An | Score | Comments |
|---|---|---|---|---|---|---|
| Example 8 | 1 | 2 | 3 | 8 | 14 | Good B & Y; No M Activity |
| Example 9 | 2 | 8 | 3 | 6 | 19 | Good Sa & Y; Psa & M |
| Example 3 | 1 | 2 | 1 | 2 | 6 | Excellent Activity |
| Example 4 | 1 | 2 | 1 | 2 | 6 | Excellent Activity |
| Example 7 | 1 | 2 | 1 | 2 | 6 | Excellent Activity |

B = bacteria; Y = yeast; M = Mold
NOTE:
The lower the score, the greater the activity.

B=bacteria; Y=yeast; M=Mold
NOTE: The lower the score, the greater the activity.

As can be clearly seen the compounds of the present invention are good antimicrobials when compared to traditional surfactants.

Detergency

Detergency was also studies. The cleanliness of hair washed in the salon in half head studies was conducted. A 5% solution of the composition of the present invention was evaluated. The person having the test run was asked to evaluate the following samples for cleanliness of the hair. The scale was 1 (poor) to 5 excellent.

Results

| Material | Result |
|---|---|
| Sodium Lauryl Sulfate | 5 |
| Sodium Laureth 2 Sulfate | 4 |
| Example 3 | 4 |
| Example 4 | 4 |

-continued

| Material | Result |
|---|---|
| Example 8 | 4 |
| Example 9 | 4 |
| Example 7 | 4 |
| APG | 2 |
| (Raw material for preparation of the products of the current invention) | |

CONCLUSION

As can be easily seen the compositions of the present invention, unlike traditional surfactants used in personal care products, are truly multi-functional materials that can be used by themselves to provide all the desirable properties of personal care products like shampoos and body washes. They are excellent conditioners, and provide outstanding wet comb properties, good detergency as well as antimicrobial properties. They are non-irritating and are derived from natural products. It is not until the process of the present invention that a singles component multi-functional surfactant was known.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claim be construed as encompassing all the features of patentable novelty which reside in the present invention, including all features which would be treated as equivalents thereof by those skilled in the art to which the invention pertains.

What is claimed is:

1. A process for cleansing and conditioning hair and skin with a self preserving composition which comprises contacting the hair and skin with an aqueous solution of composition comprising a compound selected from the group consisting of:

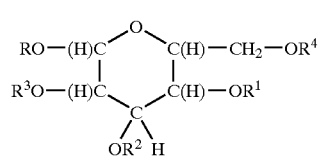

(a)

wherein;

R is alkyl having 8 to 22 carbon atoms;

$R^1$, $R^2$, $R^3$ and $R^4$ are independently selected from the group consisting of

and H, with the proviso that $R^1$, $R^2$, $R^3$ and $R^4$ are not all H;

$R^{12}$ is

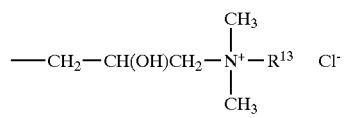

$R^{13}$ is alkyl having 8 to 22 carbon atoms; and (b)
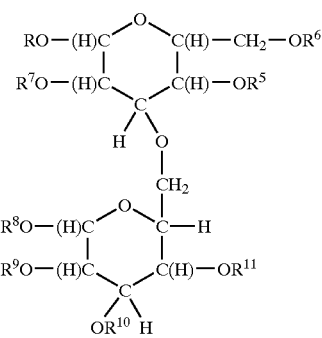

wherein; and mixtures thereof

R is alkyl having 8 to 22 carbon atoms;

$R^1$, $R^2$, $R^3$ and $R^4$, $R^5$, $R^6$, $R^7$, $R^8$, $R^9$, $R^{10}$, and $R^{11}$ are independently selected from the group consisting of

and H, with the proviso that $R^1$, $R^2$, $R^3$ and $R^4$ are not all H;

$R^{12}$ is

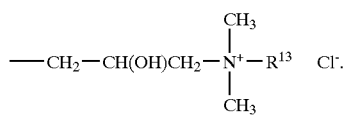

2. A process of claim 1 wherein $R^{13}$ is alkyl having 8 to 22 carbon atoms.

3. A process of claim 1 wherein $R^{13}$ is alkyl having 12 carbon atoms.

4. A process of claim 1 wherein $R^{13}$ is alkyl having 16 carbon atoms.

5. A process of claim 1 wherein $R^{13}$ is alkyl having 16 carbon atoms.

6. A process of claim 1 wherein $R^{13}$ is alkyl having 18 carbon atoms.

7. A process of claim 1 wherein $R^{13}$ is alkyl having 20 carbon atoms.

8. A process of claim 1 wherein $R^{13}$ is alkyl having 22 carbon atoms.

9. A process of claim 1 wherein $R^{13}$ is alkyl having 24 carbon atoms.

10. A process of claim 1 wherein the effective concentration ranges from 1% to 25% by weight.

11. A process of claim 10 wherein $R^{13}$ is alkyl having 8 to 22 carbon atoms.

12. A process of claim 10 wherein $R^{13}$ is alkyl having 12 carbon atoms.

13. A process of claim 10 wherein $R^{13}$ is alkyl having 16 carbon atoms.

14. A process of claim 10 wherein $R^{13}$ is alkyl having 16 carbon atoms.

15. A process of claim 10 wherein $R^{13}$ is alkyl having 18 carbon atoms.

16. A process of claim 10 wherein $R^{13}$ is alkyl having 20 carbon atoms.

17. A process of claim 10 wherein $R^3$ is alkyl having 22 carbon atoms.

18. A process of claim 10 wherein $R^{13}$ is alkyl having 24 carbon atoms.

* * * * *